(12) United States Patent
Anderson et al.

(10) Patent No.: US 7,811,222 B2
(45) Date of Patent: Oct. 12, 2010

(54) METHOD AND APPARATUS FOR TREATING PELVIC ORGAN PROLAPSE

(75) Inventors: Kimberly A. Anderson, Eagan, MN (US); James E. Cox, Corcoran, MN (US)

(73) Assignee: AMS Research Corporation, Minnetonka, MN (US)

(*) Notice: Subject to any disclaimer, the term of this patent is extended or adjusted under 35 U.S.C. 154(b) by 750 days.

(21) Appl. No.: 11/518,932

(22) Filed: Sep. 12, 2006

(65) Prior Publication Data

US 2007/0068538 A1 Mar. 29, 2007

Related U.S. Application Data

(63) Continuation-in-part of application No. 10/840,646, filed on May 7, 2004, now Pat. No. 7,351,197, and a continuation-in-part of application No. 10/834,943, filed on Apr. 30, 2004, now Pat. No. 7,500,945.

(60) Provisional application No. 60/716,110, filed on Sep. 12, 2005.

(51) Int. Cl.
*A61F 2/00* (2006.01)
(52) U.S. Cl. .................. 600/37; 600/29; 600/30
(58) Field of Classification Search ............ 600/29–32, 600/37; 606/1, 99, 104, 119, 139, 159, 190, 606/222–227
See application file for complete search history.

(56) References Cited

U.S. PATENT DOCUMENTS

| | | | | |
|---|---|---|---|---|
| 6,053,935 | A * | 4/2000 | Brenneman et al. | 606/232 |
| 7,094,199 | B2 * | 8/2006 | Petros et al. | 600/29 |
| 2002/0099259 | A1 * | 7/2002 | Anderson et al. | 600/29 |
| 2004/0039246 | A1 * | 2/2004 | Gellman et al. | 600/30 |

* cited by examiner

*Primary Examiner*—Charles A Marmor, II
*Assistant Examiner*—Carrie Dorna
(74) *Attorney, Agent, or Firm*—Jose' W. Jimenez; Kimberly K. Baxter; Gregory L. Koeller

(57) ABSTRACT

An apparatus for treating pelvic organ prolapse in a patent is provided. The apparatus includes a support portion having first and second ends. A first elongated end portion is connected to the first end of the support portion. The first elongated end portion includes a first dilator configured to attach securely with a tip of a needle. A second elongated end portion is connected to the second end of the support portion. The second elongated end portion includes a second dilator configured to attach securely with a tip of a needle. The first and second needles include a straight portion, a tip, a first radius, and a second radius distinct from the first radius. The first radius and the second radius are disposed between the straight portion and the tip. A method and kit for the treatment is further provided.

17 Claims, 19 Drawing Sheets

METHOD AND APPARATUS FOR TREATING PELVIC ORGAN PROLAPSE

RELATED APPLICATIONS

This application is a utility application claiming priority to U.S. Provisional Application 60/716,110, filed Sep. 12, 2005, the entire contents of which is incorporated by reference herein. This application is also a continuation in part of U.S. patent application Ser. No. 10/834,943 filed Apr. 30, 2004, and U.S. patent application Ser. No. 10/840,646 filed May 7, 2004 which are incorporated by reference herein.

BACKGROUND OF THE INVENTION

1. Field of the Invention

The invention relates generally to the treatment of urogenital conditions. More particularly, the invention relates to devices and surgical techniques for use in treating female pelvic organ prolapse.

2. Description of the Related Art

When intra-abdominal pressure pushes the vagina outside the body, vaginal prolapse can develop. In normal circumstances, the levator ani muscles close the pelvic floor, supporting it from below while fascia a ligaments support. Increases in abdominal pressure, failure of the muscles to keep the pelvic floor supported, and damage to the ligaments and fascia all contribute to the development of prolapse. In addition, if a woman has a hysterectomy, the vaginal angle may be altered and ligament support reduced, causing increased pressure at a more acute angle, accelerating the prolapse.

The vagina and uterus are generally composed of two different types of tissue. First, there are fibrous connective tissues that attach these organs to the pelvic walls (cardinal and uterosacral ligaments; pubocervical and rectovaginal fascia). Second, the levator ani muscles close the pelvic floor so the organs can rest on the muscular shelf. It is when damage to the muscles open the pelvic floor or during the trauma of childbirth that the fascia and ligaments are strained. Breaks in the fascia allow the wall of the vagina or cervix to prolapse downward.

A variety of factors can cause genital prolapse in women. It is thought that individual women have differing inherent strength of the relevant connective tissue. The loss of connective tissue strength may be associated with damage at childbirth, deterioration with age, poor collagen repair mechanisms, and poor nutrition. Loss of muscle strength might also be associated with neuromuscular damage during childbirth, neural damage from chronic straining, and metabolic diseases that affect muscle function. Other factors involved in prolapse include increased loads on the supportive system, as seen in prolonged lifting or chronic coughing from chronic pulmonary disease, or some disturbance in the balance of the structural support of the genital organs. Possible factors may also include obesity, constipation, and a history of hysterectomy.

Anterior vaginal wall prolapse causes the vaginal wall to fail to hold the bladder in place. This condition, in which the bladder sags or drops into the vagina, is termed a cystocele. There are two types of cystocele caused by anterior vaginal wall prolapse. Paravaginal defect is caused by weakness in the lateral supports, mainly the attachment of the bladder to the endopelvic fascia; central defect is caused by weakness in the central supports, mainly the fascial layers. A transverse defect, causing cystecele across the vagina, may also occur.

Posterior vaginal wall prolapse results in descent of the rectum into the vagina, often termed a rectocele, or the presence of small intestine in a hernia sac between the rectum and vagina, called an enterocele. There are generally four types of enteroceles based on suspected etiology. Congenital enteroceles are thought to occur because of failure of fusion or reopening of the fused peritoneal leaves down to the perineal body. Posthysterectomy vault prolapses may be "pulsion" types that are caused by pushing with increased intra-abdominal pressure. They may occur because of failure to reapproximate the superior aspects of the cardinal and uterosacral ligaments, pubocervical fascia and the rectovaginal fascia at the time of surgery. Enteroceles that are associated with cystocele and rectocele may be from "traction" or pulling down of the vaginal vault by the prolapsing organs. Finally, iatrogenic prolapses may occur after a surgical procedure that changes the vaginal axis, such as certain surgical procedures for treatment of incontinence. With regard to rectoceles, low rectoceles may result from disruption of connective tissue supports in the distal posterior vaginal wall, perineal membrane, and perineal body. Mid-vaginal and high rectoceles may result from loss of lateral supports or defects in the rectovaginal septum. High rectoceles may result from loss of apical vaginal supports. Posterior or posthysterectomy enteroceles may accompany rectoceles.

Vaginal prolapse and the concomitant anterior cystocele can lead to discomfort, urinary incontinence, and incomplete emptying of the bladder. Posterior vaginal prolapse may additionally cause defecatory problems, such as tenesmus and constipation.

Various techniques have been tried to correct or ameliorate the prolapse and its symptoms, with varying degrees of success. Nonsurgical treatment of prolapse involves measures to improve the factors associated with prolapse, including treating chronic cough, obesity, and constipation. Other nonsurgical treatments may include pelvic muscles exercises or supplementation with estrogen. These therapies may alleviate symptoms and prevent worsening, but the actual hernia will remain. Vaginal pessaries are the primary type of nonsurgical treatment. However there can be complications due to vaginal wall ulceration.

A variety of surgical techniques are used for the treatment of anterior vaginal prolapses. In the small proportion of cases in which the prolapse is caused by a central defect, anterior colporrapphy is an option. This surgery involves a transvaginal approach in which sutures are used to reapproximate the attenuated tissue across the midline of the vagina. More commonly, the prolapse is due to a lateral defect or a combination of lateral and central defects. In these instances, several surgical techniques have been used, such as a combination of an anterior colporrapphy and a site-specific paravaginal repair. Both abdominal and vaginal approaches are utilized. Biological or synthetic grafts have been incorporated to augment repair.

Similarly, the treatment of posterior vaginal prolapses may vary. If symptoms are minimal, nonoperative therapy such as changes in activities, treatment of constipation, and Kegel exercises might be appropriate. Again, both vaginal and abdominal approaches are used, involving sutures to reapproximate the attenuated tissue and possibly a biological or synthetic graft to augment the repair.

The vaginal vault may be attached to the sacrum by use of mesh or fascia in a procedure known as Sacral colpopexy. The surgery may be performed through an abdominal incision or laparoscopically, however certain undesirable complications may occur. If synthetic mesh is used, it is typically carefully customized or assembled into a special shape by the surgeon.

Sacral colpopexy can also be a tedious, challenging surgical procedure, with an average procedure length of 247 minutes reported in Winters et al., Abdominal Sacral Colpopexy and Abdominal Enterocele Repair in the Management of Vaginal Vault Prolapse, Urology 56 (Suppl 6A) (2000): 55-63. Some of this time is attributed to the time required for the surgeon to fashion the implant. In addition, it is often required to correct multiple pelvic floor abnormalities simultaneously, which further increases the duration of the surgery.

Another procedure, called sacrospinous fixation, is also used to treat vaginal vault prolapse. This procedure involves attaching the vaginal vault to the sacrospinous ligament, which requires specialized skills and has the disadvantage of tending to place the vagina in an artificial anatomical position.

It is also possible to use various sling procedures to treat prolapse conditions. A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension sutures to a point of attachment (e.g. bone) through an abdominal and/or vaginal incision. Examples of sling procedures are disclosed in U.S. Pat. Nos. 5,112,344; 5,611,515; 5,842,478; 5,860,425; 5,899,909; 6,039,686; 6,042,534; and 6,110,101.

Although serious complications associated with sling procedures are infrequent, they do occur. Complications include urethral obstruction, development of de novo urge incontinence, hemorrhage, prolonged urinary retention, infection, and damage to surrounding tissue and sling erosion.

The TVT Tension-free Vaginal Tape procedure utilizes a Prolene™ nonabsorbable, polypropylene mesh to treat incontinence. A plastic sheath surrounds the mesh and is used to insert the mesh into the patient. Abdominal and vaginal incisions are made, followed by implantation of the mesh using two curved, needle-like elements to push the mesh through the vaginal incision and into the paraurethral space. Using the procedure described elsewhere, the mesh is looped beneath the bladder neck or urethra. The sling is positioned to provide appropriate support to the bladder neck or urethra. When the TVT mesh is properly positioned, the cross section of the mesh should be substantially flat. In this condition, the edges of the mesh do not significantly damage tissue. Shortcomings and attempts to address these shortcomings and other problems associated with certain tape procedures are disclosed in PCT publication nos. PCT WO 00/74613 and PCT WO 00/74594.

Due to the tough fibrous nature of fascia and muscle tissues, forceps or similar instruments are needed to withdraw the needles through the abdominal wall. However, the smooth surface of the needles, which facilitates insertion through the tissues, prevents secure attachment of the forceps onto the needles, causing slippage or detachment of the forceps during the withdrawal procedure. Improper placement of certain meshs is also particularly troublesome. If the mesh is too loosely associated with its intended physiological environment, the mesh may be ineffective in supporting the urethra and treating incontinence. Surgeons may exacerbate certain problems by improperly attempting to adjust the tension of a sling. If insufficient adjustment force is applied, the sling will simply exhibit a memory property and return to its original, unacceptable position. As a result, surgeons are tempted to use a great deal of force in order to loosen a sling that is perceived to be too tightly associated with its intended physiological environment. If excessive force is applied, the mesh will plastically deform and the cross section of the mesh will become arcuate. Excessive deformation may also result in a lack of efficacy.

U.S. Pat. No. 6,695,855 (Gatson) describes a device for treating a prolapse by vaginal suspension. The device includes an elongated, flexible pierced material, a suture connected to the material, and a suture needle joined to the suture. The device is long enough to enable posterior suspension of the vagina at the front part of the sacrum. The other end of the device includes a distal portion having a width such that it can cover at least a large part of the posterior part of the vagina, a rounded cut-out with dimensions that enable it to be engaged around the base of the vagina on at least a large part of the lower half of the wall of the vagina. The suture is connected to the article so that it is offset sidewise in relation to the cut-out.

PCT Publication No. WO 00/27304 (Ory) discloses a suspension device for treating prolapse and urinary incontinence. The device comprises at least one filiform suspension cord with limited elasticity and at least two anchoring parts linked to the ends of the cord.

U.S. Pat. No. 5,112,344 and PCT Publication No. PCT/US02/32284 disclose surgical devices for female pelvic health procedures. The IVS TUNNELLER™ device (available from U.S. Surgical, Norwalk, Conn.) comprises a fixed delta wing handle, a hollow metal tube, and a stylet that is placeable within the tube. The stylet has a rounded plastic tip on one end and an eyelet on the other end. The device may be used to implant a polypropylene tape for infracoccygeal sacropexy and other surgical procedures. A single rigid, hollow, metal tube is associated with the IVS TUNNELLER™ device. This tube passes through two separate regions of the patient's body with the attendant risk of cross-contamination. The outer diameter is also relatively large (about 0.25 inch) with the attendant risk of tissue damage due to such large diameter. The polypropylene tape supplied with the IVS TUNNELLER™ is of a thin, rectangular shape and is not believed to be optimally sized and shaped to afford concomitant procedures such as enterocele, cystocele, and/or rectocele repairs.

There is a need for a minimally invasive yet highly effective device and method that can be used to treat pelvic organ prolapse with minimal or no side effects. Such a device should reduce the complexity of procedures that are currently available while being biocompatible, adjustable, and non-toxic. Treatment methods using the device should reduce pain, operative risks, infections and post operative hospital stays, and generally improve a patient's quality of life.

SUMMARY OF THE INVENTION

The present invention is directed to an apparatus for treating pelvic organ prolapse in a patients. The apparatus includes a central support portion having multiple configurations of ends. A first elongated end portion is connected to said first end of said support portion. The first elongated end portion includes a first dilator configured to attach securely with a tip of a needle. A second elongated end portion is connected to said second end of said support portion. The second elongated end portion includes a second dilator configured to attach securely with a tip of a needle. The first and second needles include a straight portion, a tip, a first radius, and a second radius distinct from the first radius. The first radius and the second radius are disposed between the straight portion and the tip.

The method of treatment is one that allows the operator to know the location of the instruments, as final passage of the needle is aided by the operator's use of his finger, making the method less risky for the patient. The apparatus and method is convenient for the operator, in that the apparatus is relatively simple to operate and contained within the described kit. The sling portion is relatively extensible compared to the prior art. The needle is of a small diameter which reduces the risk of trauma.

The method for repairing pelvic organ prolapse in a patient generally includes the steps of using a first needle to establish a first pathway in tissue on a first side of said prolapsed organ. The pathway extends between an external perirectal region to a region of an ischial spine of the patient. The first needle comprises a tip, a straight portion, a first radius, and a second radius distinct from the first radius. The first radius and the second radius are located between the straight portion and the tip. The method also includes the step of using a second needle to establish a second pathway in tissue on a contralateral side of said prolapsed organ. The pathway extends between an external perirectal region to a region of an ischial spine of the patient. The second needle comprises a tip, a straight portion, a first radius, and a second radius distinct from the first radius. The first radius and the second radius are located between the straight portion and the tip. The method also includes the step of positioning a support member in a position to reposition a prolapsed organ in a organ's anatomically correct location. The support member comprises a support portion having a first and second end, first end portion, and second end portion. The first end portion and second end portion are respectively attached to the first end and the second end. Next, the method includes connecting the end portions to the tips of the respective needles and introducing the first end portion through the first pathway by removing the first needle from the first pathway, and introducing said second end portion through said second pathway by removing the second needle from the second pathway. Lastly, the method includes the step of adjusting the first end portion and the second end portion so that the support member is in a therapeutic relationship to a tissue of the prolapsed organ that is to be supported.

In another embodiment, the invention includes a kit for repairing pelvic organ prolapse in a patient. The kit includes a support member comprising a support portion and two end portions. At least one of the end portions further comprises a removable plastic sheath. A first needle includes a first handle, a first tip, a first radius, and a second radius, wherein the first needle is configured to atraumatically form a first pathway through tissue adjacent to said prolapsed organ. The pathway extends between an external perirectal region and a region of an ischial spine of the patient. A second needle includes a second handle, a second tip, a first radius, and a second radius. The second needle is configured to atraumatically form a second pathway through tissue adjacent to the prolapsed organ.

In yet another embodiment, the invention includes the steps of establishing a first pathway between the external perirectal region of the patient and the region of the ischial spine space in tissue on one side of the prolapsed organ, and establishing a second pathway in tissue on the contralateral side of the prolapsed organ. A support member including a central support portion and two end portions is positioned beneath the prolapsed organ in such a way as to allow repositioning of the organ into its anatomically appropriate location. The end portions of the support member are introduced through the respective tissue pathways. The end potions are adjusted so that the support member is located in a therapeutic relationship to the prolapsed organ that is to be supported.

An alternative embodiment of the invention includes a method directed to treatment of posterior vaginal prolapse. In other embodiments, the method is directed to treatment of vaginal vault prolapse, enterocele, rectocele, or a combination of more than one of these conditions. In another embodiment, the step of establishing the two tissue pathways between the external perirectal region and the region of the ischial spine of the patient, includes the steps of making a midline incision across the vagina to create access to the region of the ischial spine, through sharp and blunt dissection, and making an incision lateral and posterior to the rectum in the skin of a buttocks. A needle is passed from the incision lateral and posterior to the rectum toward the vaginal incision. The tip of the needle is palpated distal and inferior to the ischial spine and then passed through the coccygeous muscle. This step is performed on a first side, then on the contralateral side.

Further, in another embodiment, the step of positioning a support member in a position to support the prolapsed organ in its anatomically correct position includes the step of connecting the support member to the tip of the passed needle, as disclosed in U.S. Pat. No. 6,652,450, which is incorporated by reference. The step of introducing the end portions through the tissue pathways includes the step of retracting back through the respective pathways a needle to which the end portions have been connected. The step of adjusting the end portions so that the support member is in a therapeutic relationship to the prolapsed vagina that is to be supported further includes the steps of attaching the support member to the vaginal wall with sutures, ensuring the vaginal vault is in an appropriate anatomical position, removing the sheath, and adjusting the support member by manipulation of the end portions.

The present invention further provides an apparatus for treatment of pelvic organ prolapse. The apparatus broadly includes a support portion with two ends, for placement in a therapeutically effective position, and two elongated end portions connected respectively to each end of the support portion.

In one embodiment of the invention, the apparatus includes repositioning means for effecting tightening or loosening of the apparatus without adversely affecting its therapeutic efficacy. According to an embodiment, the repositioning means includes at least one filament threaded along at least one end portion. The repositioning means may include at least one removable plastic sheath on at least one end portion, wherein the sheath is configured to affect tightening of the apparatus when the apparatus is partially implanted and the sheath is removed.

In one embodiment, the support portion of the apparatus is substantially rectangular, with two long sides and two short sides. The end portions are connected to the first and second long sides, respectively.

In another embodiment, the apparatus is substantially one tape, in which the support portion is a wider center section, relative to the two end portions, in which the support and the end portions are substantially one tape. Such an embodiment would allow for easier and more secure suture attachment.

In another embodiment, the support portion is of a different material in order to provide for better suture retention.

In another embodiment, the support portion of the apparatus includes first and second elongated portions and means for inserting and securing a biological graft material between the first and second elongated portions.

In another embodiment, the support portion of the apparatus is made from a polypropylene monofilament mesh. At least one of the end portions is made from a polypropylene monofilament mesh according to one embodiment.

In one embodiment, at least one of the end portions of the support member includes a connector configured to attach securely with the end of the needle.

Another aspect of the present invention is a mesh implant that is self-fixating, without the need to pass through an extensive amount of tissue. In a preferred embodiment, lateral and central support for the prolapsed organ (such as a cystocele) is provided with one structure. The implant of this embodiment includes a middle section structured to provide support for the prolapsed organ (such as the anterior vaginal wall in a cystocele), with one or more pairs of legs extending from left and right aspects of the middle section. The implant may be made from a single material or from a combination of materials. The implant can be fixed via a tissue anchor on one or more of the legs. In this embodiment, the legs are pushed up to the arcus where they are fixed.

Prolapsed organs, including cystocele, are graded based on their severity. For example, a grade 1 cystocele is mild, with the bladder drooping only a short way into the vagina. More severe cystocele are graded up to a grade 4 custocele. In the mesh support having one or more pairs of legs, the number of legs varies based on the severity of the prolapse. For example, a grade 2-3 prolapse may require one or two pairs of legs to provide adequate support, while a grade 3 or 4 prolapse may require three or more pairs of legs. In addition, posterior legs are provided to allow the surgeon to attach the vault in the case of a total anterior repair. These arms associated with the vault can be attached to the uterosacral ligaments.

The self-fixating mesh implant may be placed using needles and dilators, as discussed herein for other embodiments of the present invention. The dilator may be designed in such a fashiob to remain in the body and serve as a tissue anchor until sufficient tissue has ingrown into the mesh. The dilator may also be bioresorbable. The legs of the implant are extended outward from the middle portion to the arcus tendineus of the patient, to which the legs are fixed. Some legs are implanted via a transobturator approach, such as the approach described in U.S. Pat. No. 7,070,556, the contents of which are herein incorporated by reference. Likewise, the legs may be implanted via a transvaginal, as described herein, going to the arcus or the obturator foramen, but not out of the body through a skin incision. The present invention also provides a needle for the placement of such a self-fixating implant. The needle adapts to the dilator to allow it to be pushed into place and released. The needle may include markers to indicate the penetration depth and corresponding anatomical placement areas corresponding to the number of legs in the mesh.

The present invention also provides a kit including the elements for practice of the present method. The kit broadly includes a means for repositioning and supporting the prolapsed organ in a physiologically correct position and a means for attaching said repositioning and supporting means to an appropriate anatomical structure.

In yet another embodiment, the kit of the present invention includes a support member including a support portion and two end portions, wherein at least one end portion includes a support portion and two end portions, wherein at least one end portion includes a removable plastic sheath, first and second needles configured to atraumatically form first and second pathways through tissue adjacent to the prolapsed organ, respectively, and handles for directing the needles.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
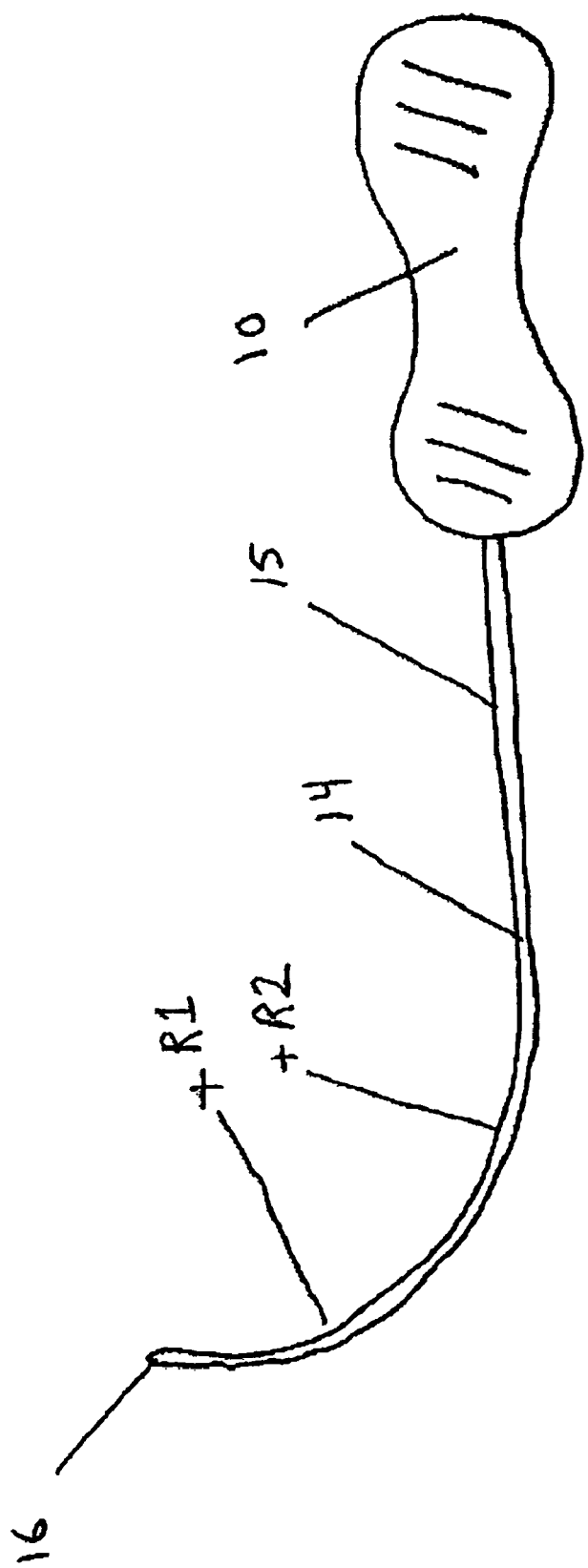
FIG. 1 is a side perspective view of a multi radii needle.

Referring now to the drawings, wherein like reference numerals designate identical or corresponding parts throughout the several views, FIG. 1 shows a needle 14 and handle 10 suitable for use in the present invention. Needle 14 terminates in a tip 16. Needle 14 comprises a generally straight section 15 near handle 10. In one embodiment, the straight section 15 shown in FIG. 1 is between about 4 inches and about 8 inches, preferably between about 5 inches and about 7 inches, more preferably between about 5.5 inches and about 6.5 inches.

The portion of needle 14 between straight section 15 and tip 16 includes a multi radii bend defined by a first radius R1 and a second radius R2, distinct from the first radius. The first radius R1 is generally between about 2 inches and about 4 inches, preferably between about 2.5 inches and about 3.5 inches. The second radius R2 is generally larger than R1. In one embodiment, R2 is between about 4 inches and about 6 inches, preferably between about 4.5 inches and 5.5 inches. This multi-radii bend allows for at least 1 cm of additional curvature of tip 16 for easier final passage past the ischial spine of a patient. It also enables an easier connection between the tip 16 and a mesh support structure. Moreover, the multi-radii bend provides a physician with better control of the tip 16 during a procedure.

Figure 2:
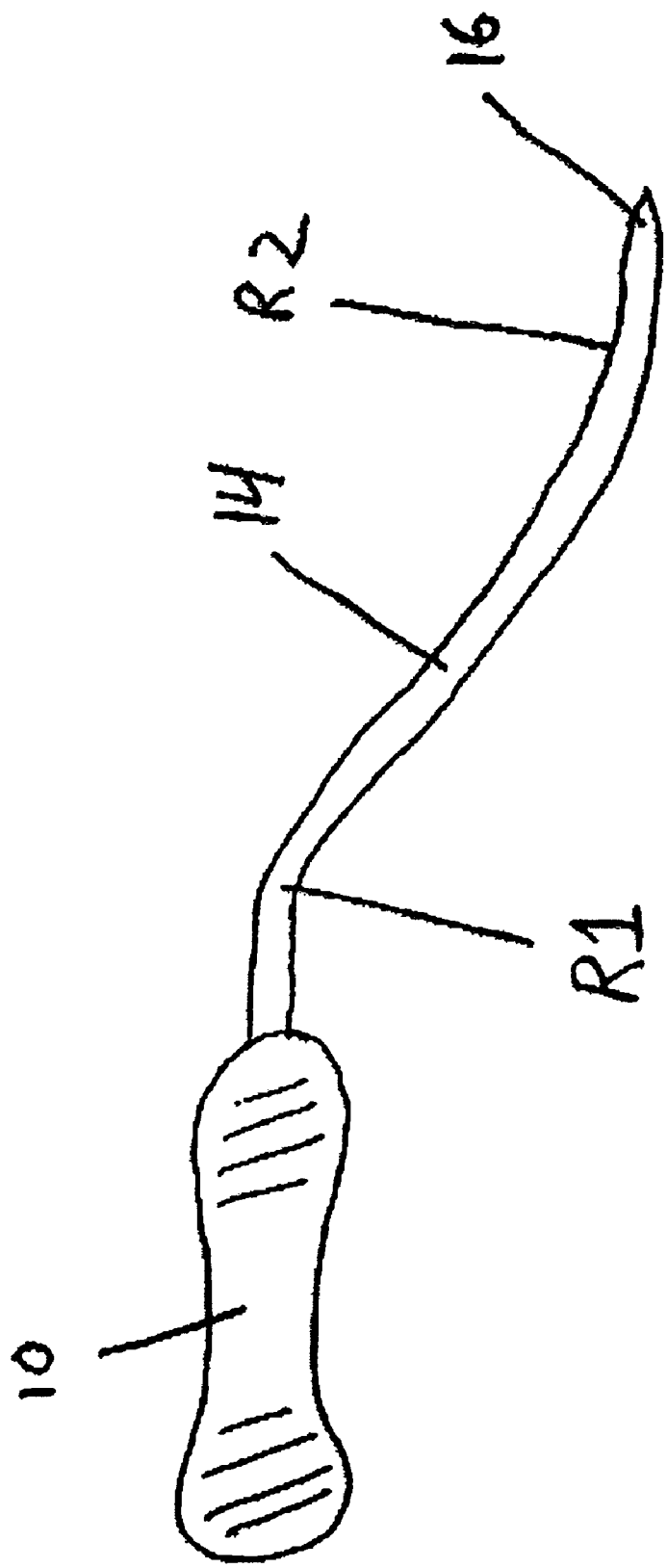
FIG. 2 is a side perspective view of an alternative embodiment of a multi radii needle.

FIG. 2 shows a needle 14 with an alternative multi-radii configuration. In this configuration, first radius R1 is on the opposite side of the needle 14 from the second radius R2. As shown in FIG. 2, first radius R1 is smaller than the second radius R2. The tip 16 of needle 14 generally lines in a line parallel to the line disposed within handle 10.

Figure 3:
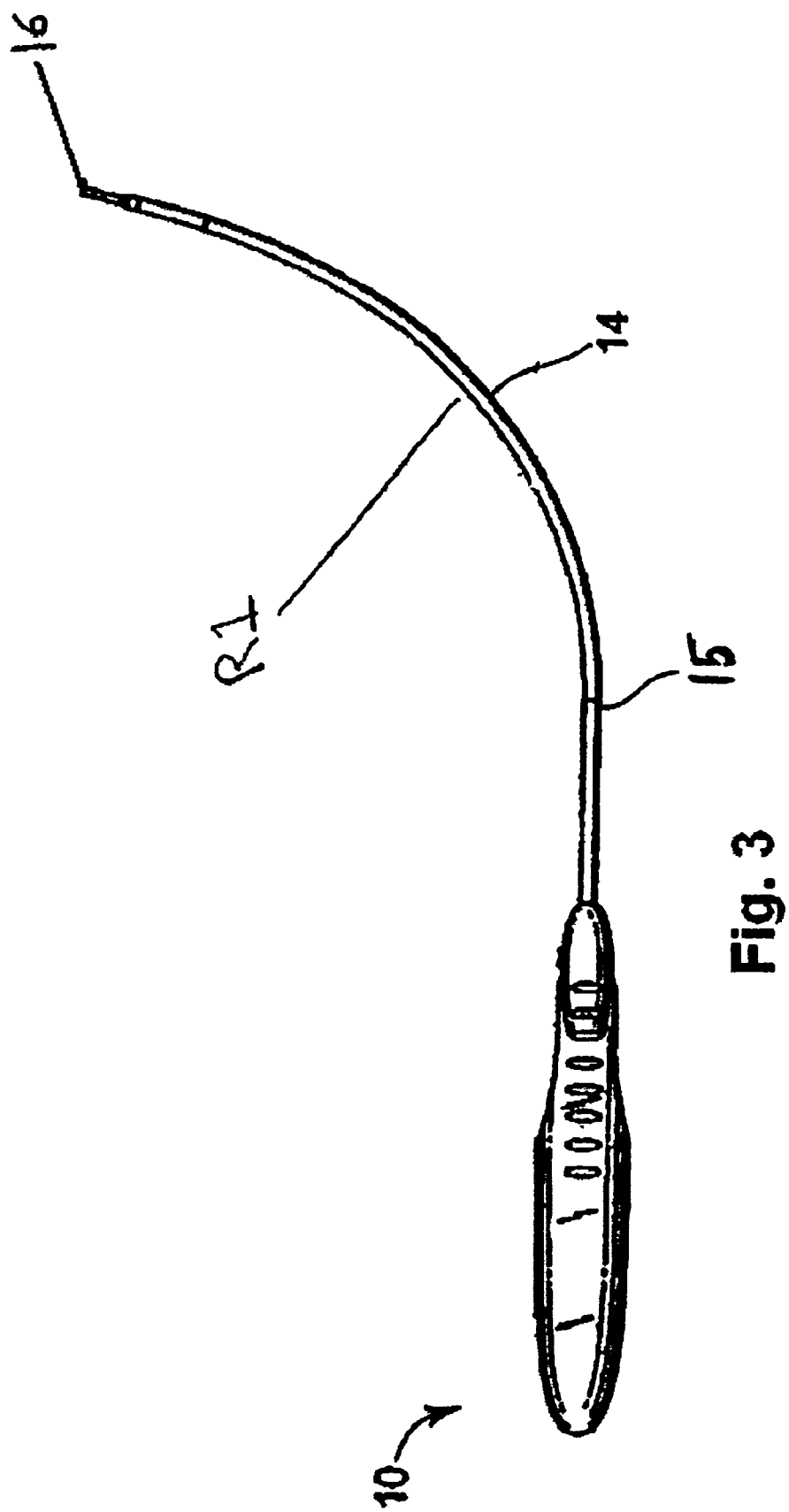
FIG. 3 is a side perspective view of another alternative embodiment of a needle.

FIG. 3 shows a needle 14 with a single-radii configuration. In this configuration, needle 14 forms a single radius R1 which terminates at tip 16. Straight section 15 is disposed between handle 10 and the portion where radius R1 begins. The tip 16 of needle 14 lines in a line generally skewed from the line disposed within handle 10.

Figure 4:
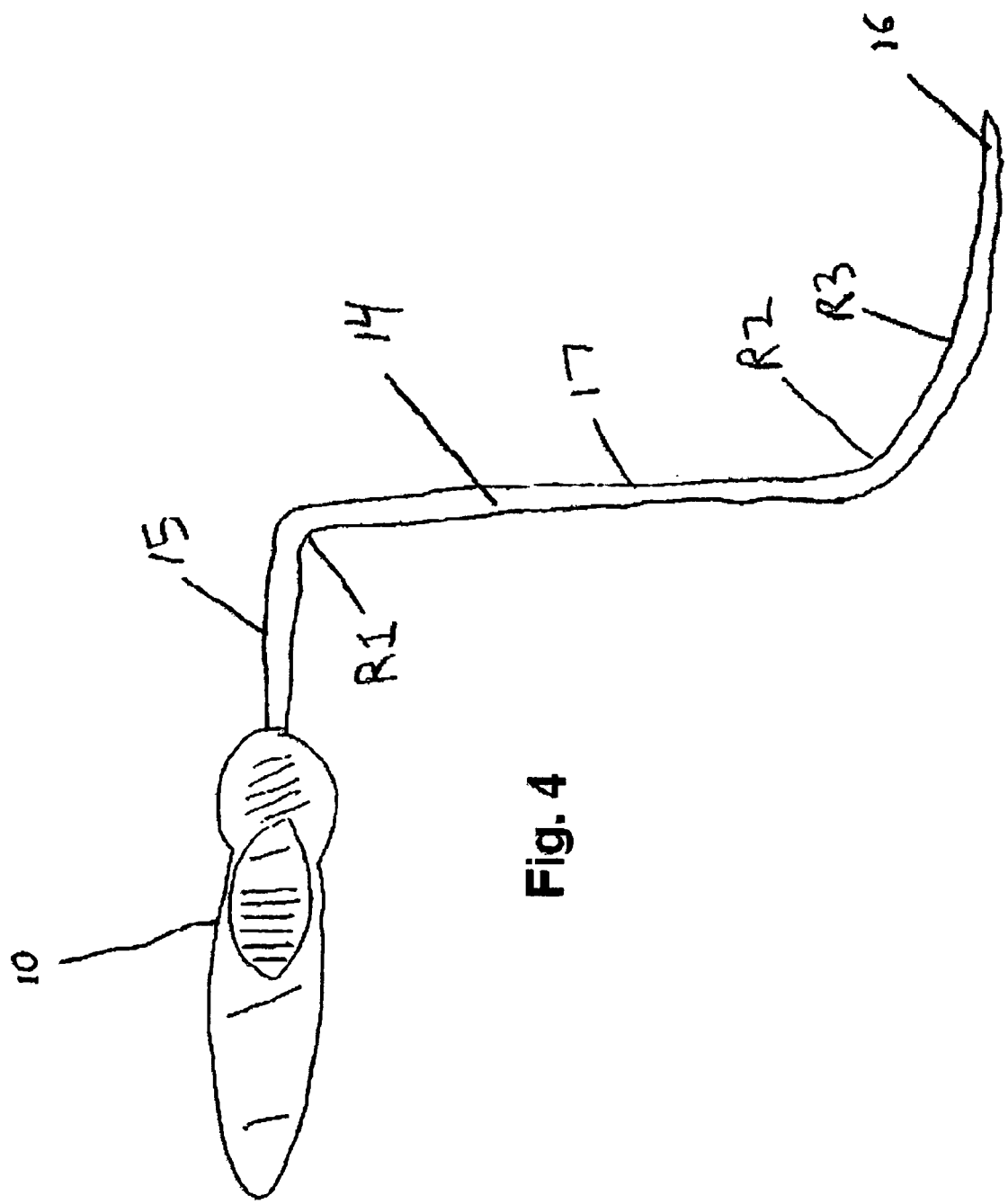
FIG. 4 is a side perspective view of yet another alternative embodiment of a multi radii needle.

FIG. 4 shows an alternative embodiment of a needle 14 which includes three radii R1, R2, and R3. In this embodiment, needle 14 is attached to handle 10 and terminates in tip 16. A first radius is disposed between straight section 15 and straight section 17. Straight section 15 is disposed between handle 10 and first radius R1. Second radius R2 and third radius R3 is disposed between straight section 17 and tip 16. First radius R1 is on the opposite side of the needle from second radius R2 and third radius R3. Moreover first radius is smaller than second radius R2 and third radius R3. This enables straight section 15 to be approximately perpendicular to straight section 17. The tip 16 of needle 14 lies in a line generally parallel to the line disposed in handle 10.

Figure 5:
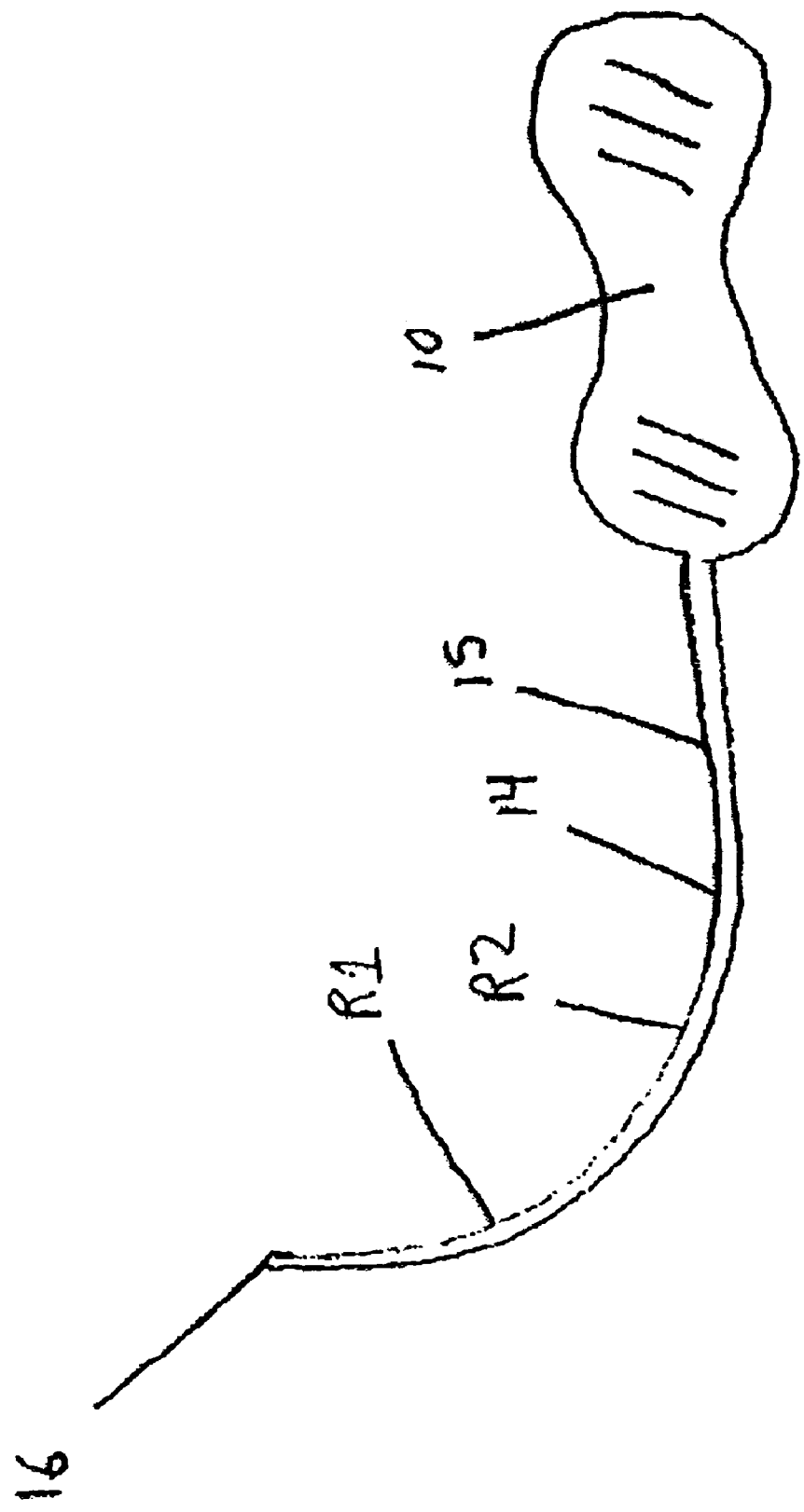
FIG. 5 is a side perspective view of a multi radii needle with short needle shank.

FIG. 5 shows an alternative embodiment of the needle shown in FIG. 1. FIG. 5 shows a needle 14 which terminates in a tip 16. Needle 14 comprises a generally straight section 15 near handle 10. The straight section 15 of the needle in FIG. 5 is at least 2 cm shorter than the straight section of the needle shown in FIG. 1. In one embodiment, the straight section 15 shown in FIG. 5 is between about 3 inches and about 7 inches, preferably between about 4 inches and about 6 inches, more preferably between about 4.5 inches and about 5.5 inches.

With continued reference to FIG. 5, the portion of needle 14 between straight section 15 and tip 16 includes a multi radii bend defined by a first radius R1 and a second radius R2, distinct from the first radius. The first radius R1 is generally between about 2 inches and about 4 inches, preferably between about 2.5 inches and about 3.5 inches. The second radius R2 is generally larger than R1. In one embodiment, R2 is between about 4 inches and about 6 inches, preferably between about 4.5 inches and 5.5 inches. This multi-radii bend allows for at least 1 cm of additional curvature of tip 16 for easier final passage past the ischial spine of a patient. It also enables an easier connection between the tip 16 and a mesh support structure. Moreover, the multi-radii bend, coupled with the shortened straight section 15, provides a physician with increased control of the tip 16 during a procedure. Furthermore, the shortened straight section 15 more easily prevents flexure of the needle 14 by providing increased rigidity.

A variety of needle designs and/or configurations disclosed herein may be used. However, all references hereinafter will be made to the dual radii needles of FIG. 1 and FIG. 5 in the spirit of brevity and reader convenience.

Overall, the shape of the needle 14 should facilitate and provide controlled passage of the needle 14 through tissue as required. The ends or tip of the needle 14 are generally not sharpened, but may be tapered to afford easy passage through tissue while providing a blunt surface that avoids cutting sensitive tissue such as the bowel. It is preferred that the diameter of the needle 14 be slightly larger relative to the prior art to reduce tissue trauma and make palpation easier. In one embodiment, the diameter of needle 14 is between about 0.100 inches and about 0.150 inches, preferably between about 0.120 inches and about 0.130 inches, more preferably about 0.125 inches.

The needle 14 is made of a malleable, yet durable, biocompatible surgical instrument material such as, but not limited to, stainless steel, titanium, Nitinol, polymers, plastics and other materials, including combinations of materials. The needle 14 should have sufficient structural integrity to withstand the various forces (e.g., forces caused by dilator attachment, cystoscopy aid passage, and penetration/passage of the needle 14 through the various tissues) without undergoing any significant structural deformation.

FIGS. 1-5 show needle tip 16. Needle tip 16 is optionally adapted to connect securely to a connector on the end of a sheath associated with as least one of the end portions of a support member. Many different configurations of such a system are known in the art and within the scope of the present invention. Several configurations are disclosed in U.S. Pat. No. 6,652,450, which is incorporated herein by reference.

Figure 6:
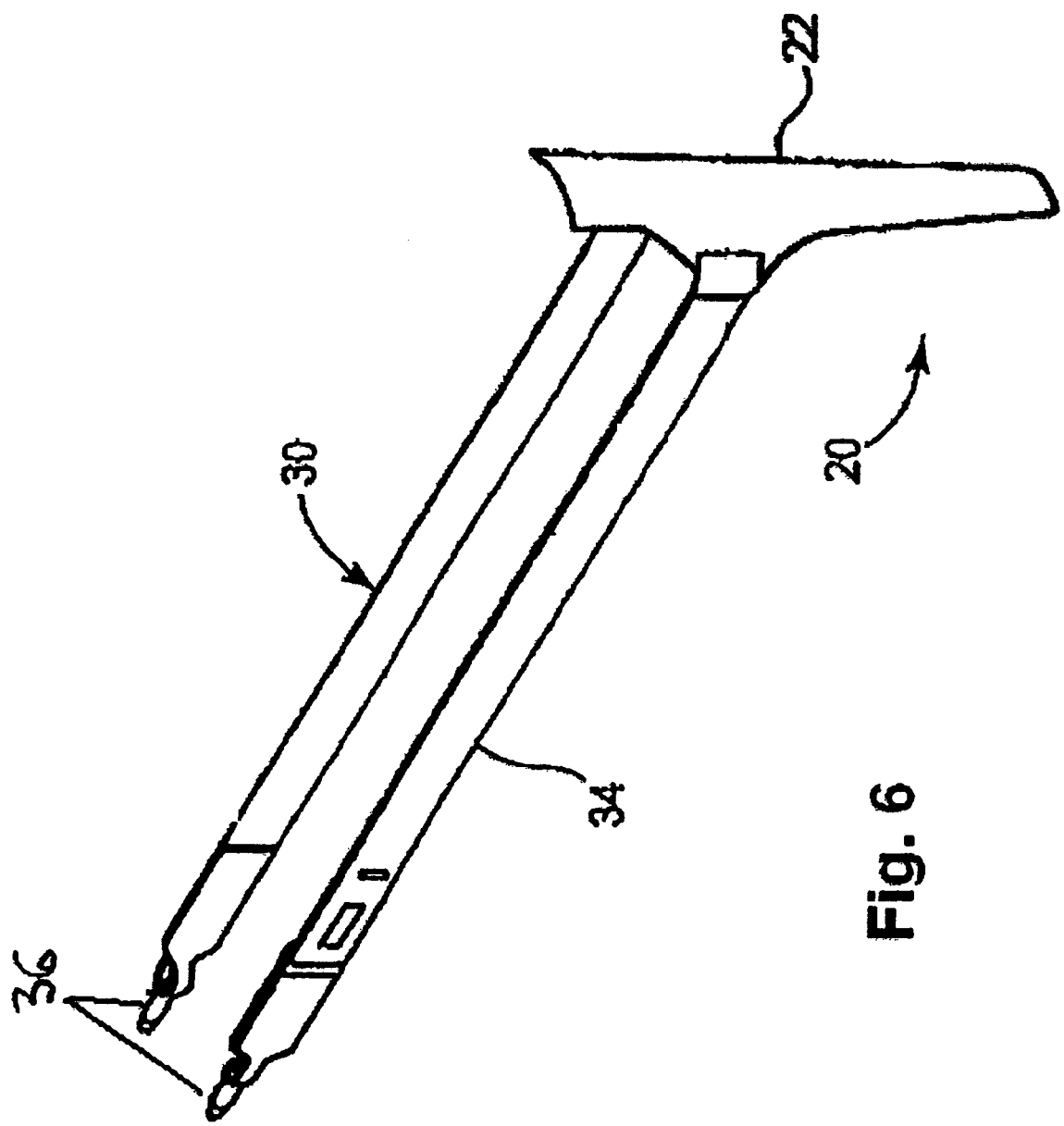
FIG. 6 is a perspective view of the support member combined with a sheath and a dilator.

Following passage through the pathways, the needle tip is connected to a support member of the present invention. Following proper positioning of the support member, the needles are retracted back through the skin incision, carrying the end portions of the support member to the skin incision. FIG. 6 shows an embodiment of the support member 20 of the present invention. The support member 20 is a mesh fabric including the support portion 22 and two end portions 30 and 34. In various embodiments of the invention, the support member may be a one piece mesh with the support portion substantially continuous with the end portions.

Many different types of mesh are known in the art and may be suitable for the present invention. Both biocompatible absorbable and non-absorbable yarns can be used to make the surgical meshes required. Suitable non-absorbable materials for use in the present invention include, but are not limited to, cotton, linen, silk, polyamides (e.g. polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terephthalate, copolymers and blends thereof), fluoropolymers (e.g. polytetrafluoroethylene and polyvinylidene fluoride) polyolefins (e.g. polypropylene including isotactic and syndiotactic polypropylene and blends thereof, as well as, blends composed predominately of isotactic or syndiotactic polypropylene blended with heterotactic polypropylene (such as are described in U.S. Pat. No. 4,557,264 issued Dec. 10, 1985 assigned to Ethicon, Inc. hereby incorporated by reference) and polyethylene (such as is described in U.S. Pat. No. 4,557,264 issued Dec. 10, 1985 assigned to Ethicon, Inc. hereby incorporated by reference)) and combinations thereof.

Suitable absorbable materials for use as yarns include but are not limited to aliphatic polyesters which include but are not limited to homopolymers and copolymers of lactide (which includes lactic acid and meso lactide), glycolide (including glycolic acid), epsilon.-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate, hydroxyvalerate, 1,4-dioxepan-2-one (including its dimmer 1,5,8,12-tetraoxacyclotetradecane-7,14-dionc), 1,5-dioxepan-2-one, 6,6-dimethyl-1,4-dioxan-2-one and polymer blends thereof.

In the present invention, the mesh is preferably fabricated from a 4.0 mil diameter monofilament polypropylene yarn by employing methods known in the art and described in "Warp Knitting Production" by Dr. S. Raz, Melliand Textilberichte GmbH, Rohrbacher Str. 76, D-6900 Heidelberg, Germany (1987), the contents of which are incorporated by reference herein. U.S. Pat. No. 6,638,284 is also herein incorporated by reference in its entirety.

A preferred mesh for use in the present invention is a polypropylene mesh possessing a thickness of about 0.021 inches, has about 27.5 courses per inch, and 13 wales per inch. It has three bar warp knit construction with a bar pattern set-up of #1: 1/0, 2/3, 2/1, 2/3, 1/0, 1/2, 1/0, 1/2: #2: 1/0, 2/3, 2/3, 1/0: #3: 2/3, 1/0, 1/2, 1/0, 2/3, 2/1, 2/3, 2/1.

In an alternative embodiment, the apparatus of the present invention can have different mesh knits in the support member and the end portions. Such a construction would allow use of the optimum knit for support or anchoring. Such an apparatus could be manufactured by use of variable knitting and/or variable heat-setting techniques.

Figure 7:
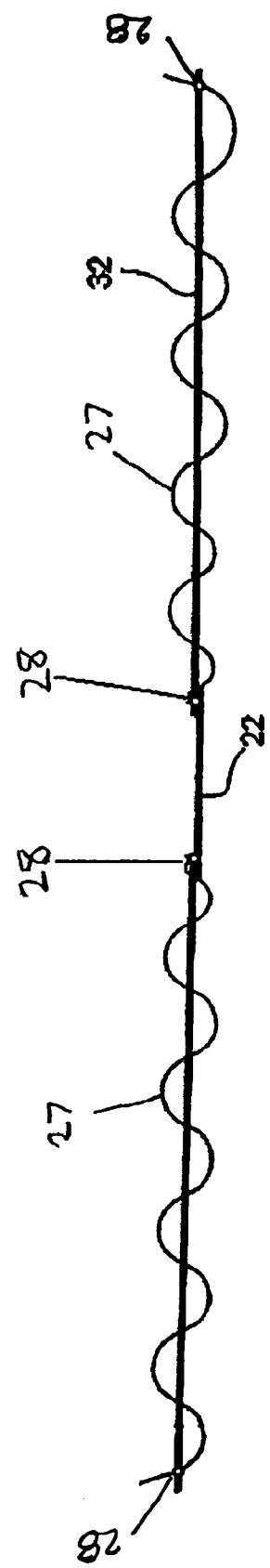
FIG. 7 is a side view of the support member showing a filament tension control member.
Figure 8:
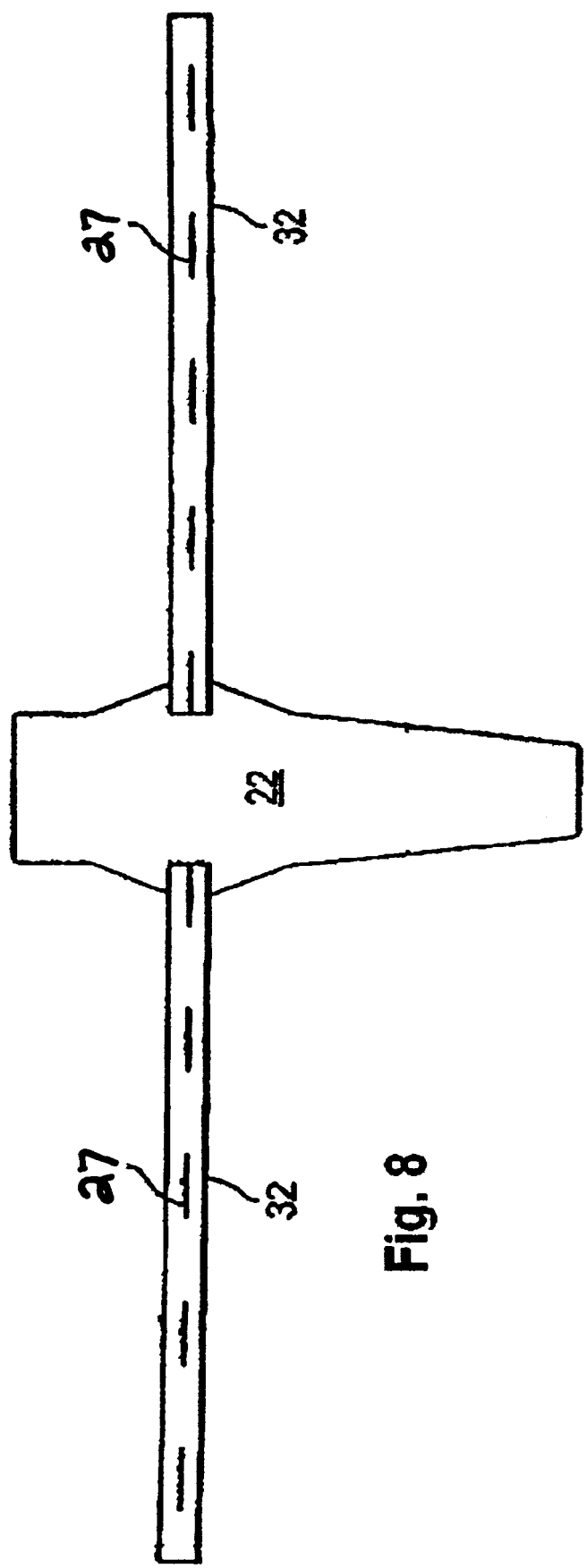
FIG. 8 is a top view of an embodiment of the support member showing a filament tension control member.

FIGS. 7 and 8 illustrate the tension control member 27. The tension control member 27 serves as a repositioning means to effect tightening or loosening of the apparatus without adversely affecting the therapeutic efficacy of the apparatus.

Several different embodiments of tension control member 27 are within the scope of the present invention. In the illustrated embodiment, tension control member 27 is a monofilament fiber woven into the support member and attached to the support member via attachment points 28 located near the support portion 22 of the support member.

Other attachment configurations for the tension control member are also included within the scope of the claimed invention. Several variations of the tension control member are described in U.S. Pat. No. 6,652,450, which is incorporated by reference in its entirety.

The tension control member enables surgeons to easily increase (tighten) or decrease (loosen) the support member tension during the surgical procedure. To reduce the tension of the support member using the tension control member 27, the surgeon contacts the support member and tension control member 27 adjacent the prolapsed organ and pulls away from the organ. The tension of the central portion may be increased by grasping the support member and tension control member 27 above the vaginal incision and pulling upward. One or both end portions of the support member, and tension control member may be grasped to increase the tension of the support member, effecting tightening by pulling the end portions out at the incisions in the buttocks. Affording adjustment of the support member facilitates proper support member placement and helps avoid complications such as recurrence and tissue erosion arising out of improper placement.

The individual fibers or filaments comprising the tension control member may be extruded, woven, braided, spun, knitted, non-woven or have other similar configurations. Tension control member properties, such as tensile strength, elongation at break point, stiffness, surface finish, etc., may be similar to or different from those of the support member and may vary along the length of the support member.

Figure 9:
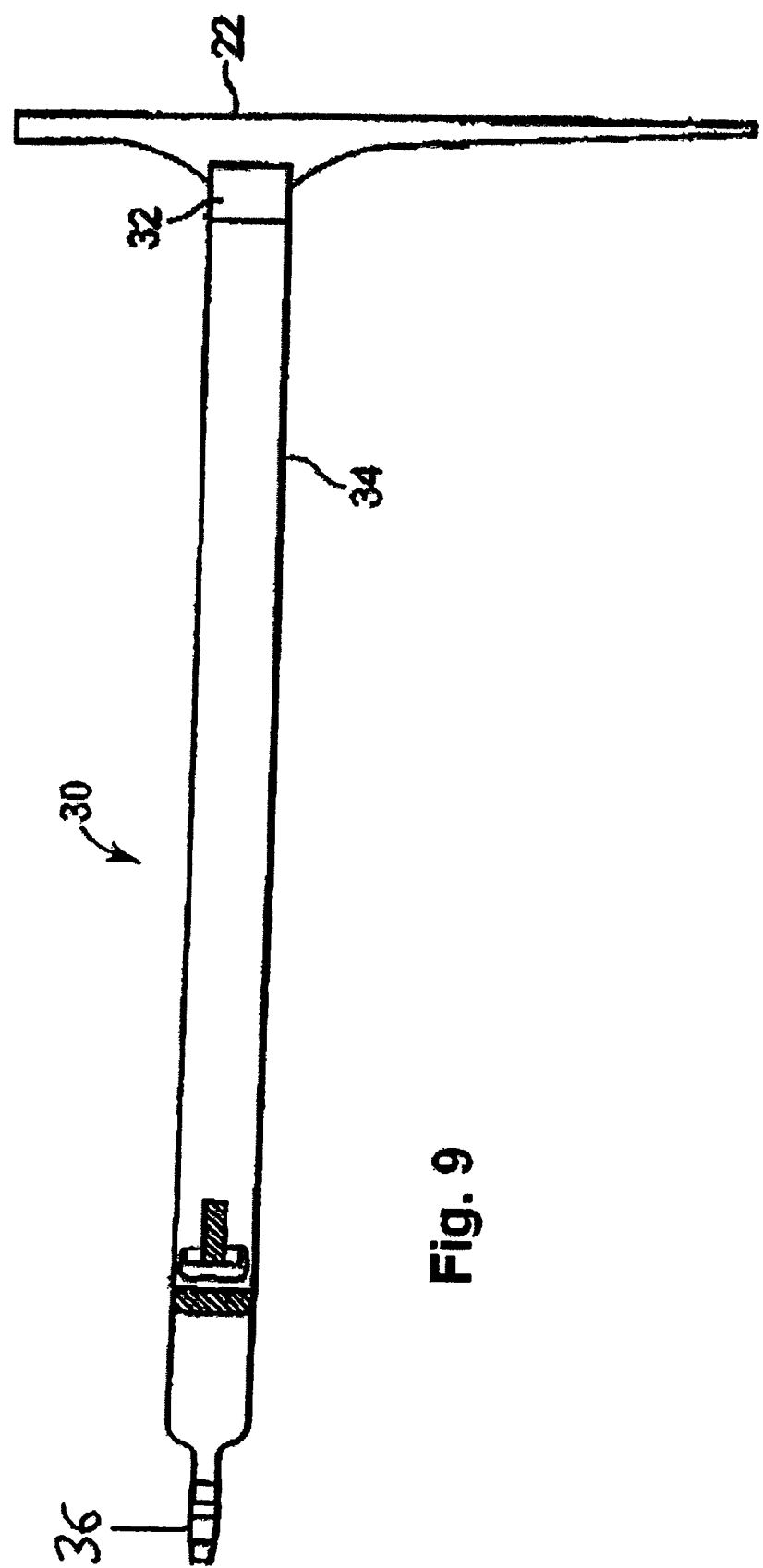
FIG. 9 is a side perspective view of the support member combined with a sheath and a dilator.

FIGS. 6 and 9 show a mesh/sheath assembly. In this preferred embodiment, the end portions 32 of the support member are substantially enclosed by a sheath 34. The sheath acts to ease the passage of the mesh end portions 32 through the tissue and to protect the mesh from deformation. The sheath 34 further serves to maintain the mesh in a more sterile condition because, prior to removal of the sheath, the mesh itself has not contacted the vagina. The sheath 34 further provides a means of adjusting the positioning of the support member through manual manipulation of the sheath 34 before their removal. The sheath 34 may optionally further comprise a connecting mechanism to affect a secure attachment to the end of the needle. Such mechanism may be one of many different configurations known in the art, such as those keying configurations disclosed in U.S. Pat. No. 6,652,450, which is incorporated by reference. A preferred embodiment comprises a loop for attachment of the end portions to the needle. This loop is enlarged to allow a surgeon to place his finger through the loop and push the connector onto the needle.

Figure 10:
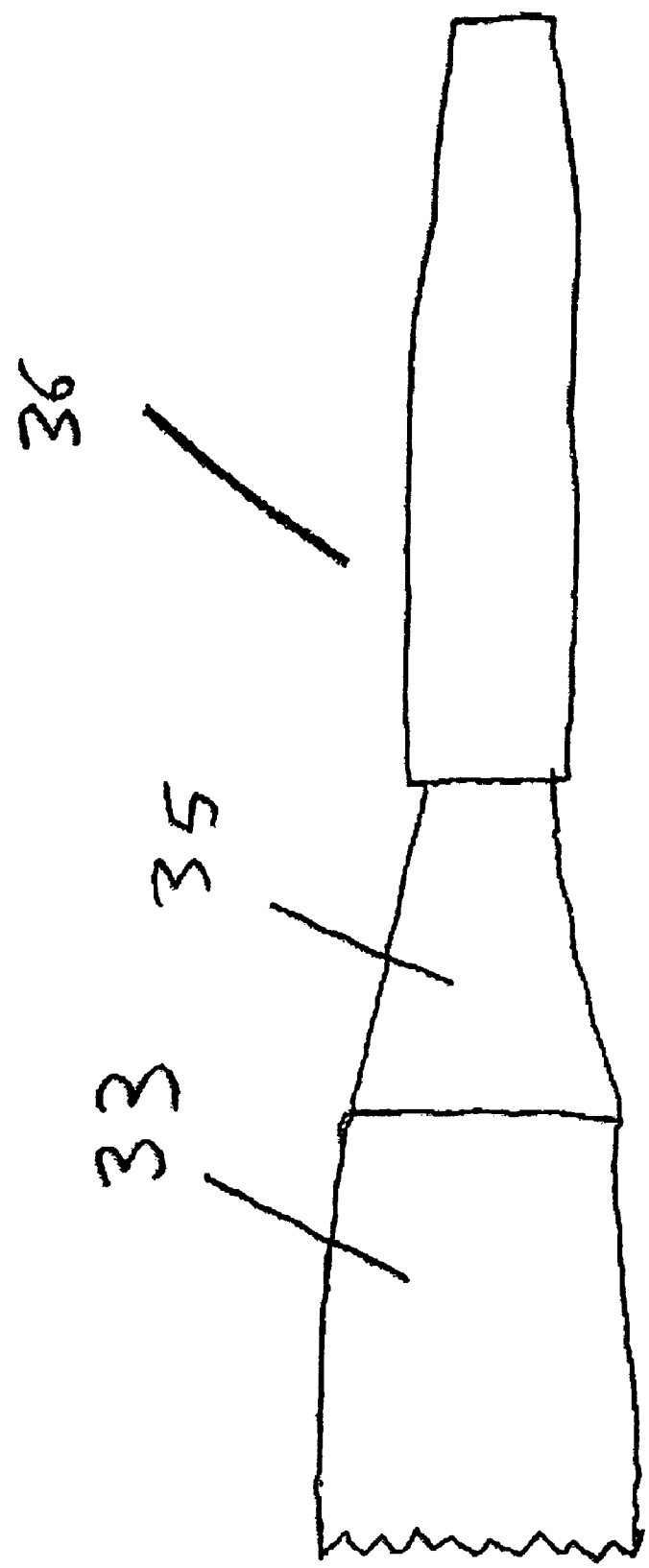
FIG. 10 is a side view of a dilator with low-profile riveted connection.

FIG. 10 shows the attachment of the dilator 36 to the end portion 33 of the support member. A transition zone 35 is disposed between end portion 33 and dilator 36. Transition zone 35 is comprised of a riveted synthetic cape which provides a tapered transition from end portion 33 to dilator 36. In a preferred embodiment, transition zone 35 is at least partially disposed inside dilator 36. This configuration helps minimize snagging of pelvic tissue on the transition zone 35 and end portion 33 as the dilator 36 is pulled through tissue.

Figure 11:
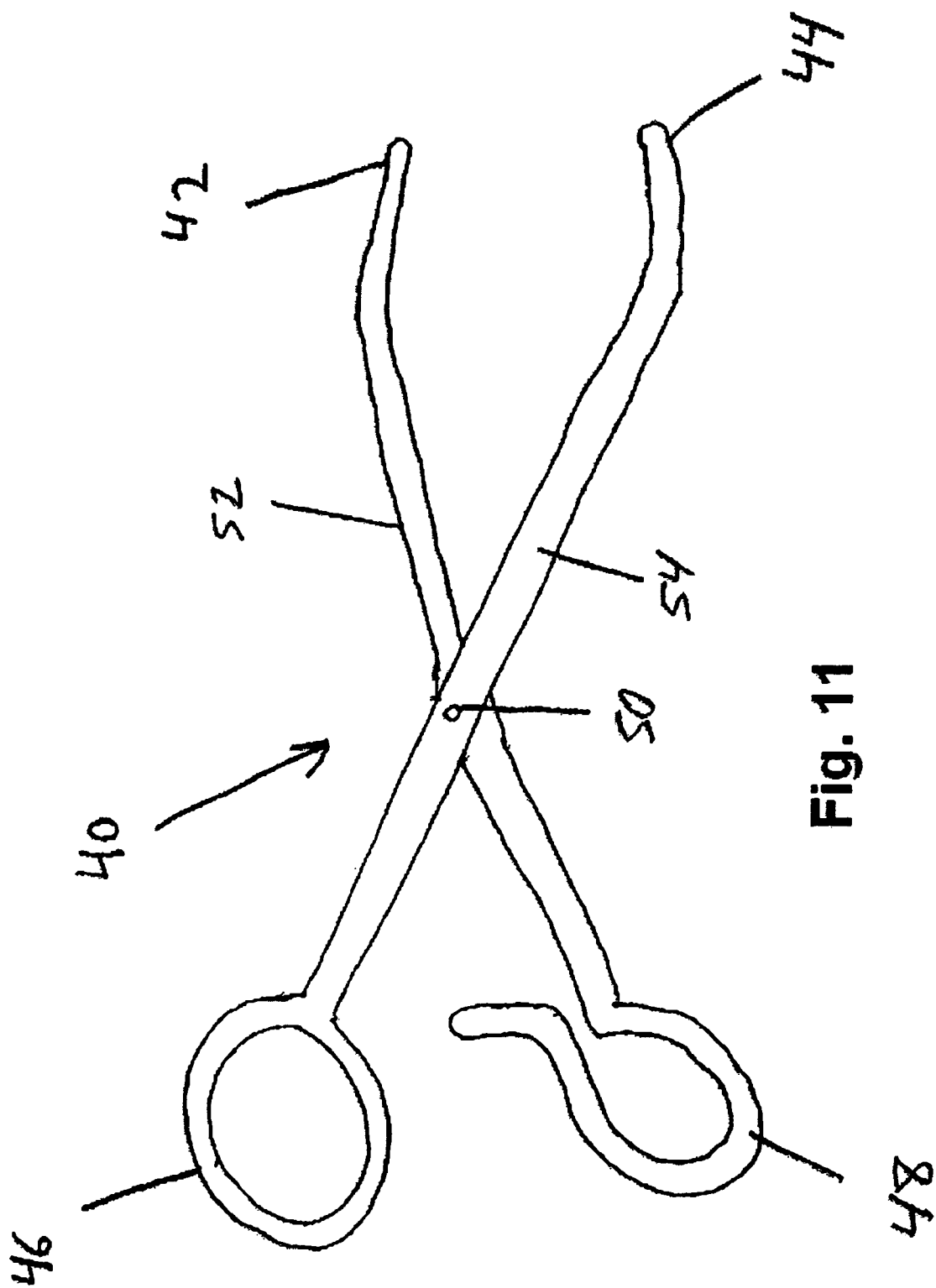
FIG. 11 is a side view of a dilator connection tool.
Figure 12:
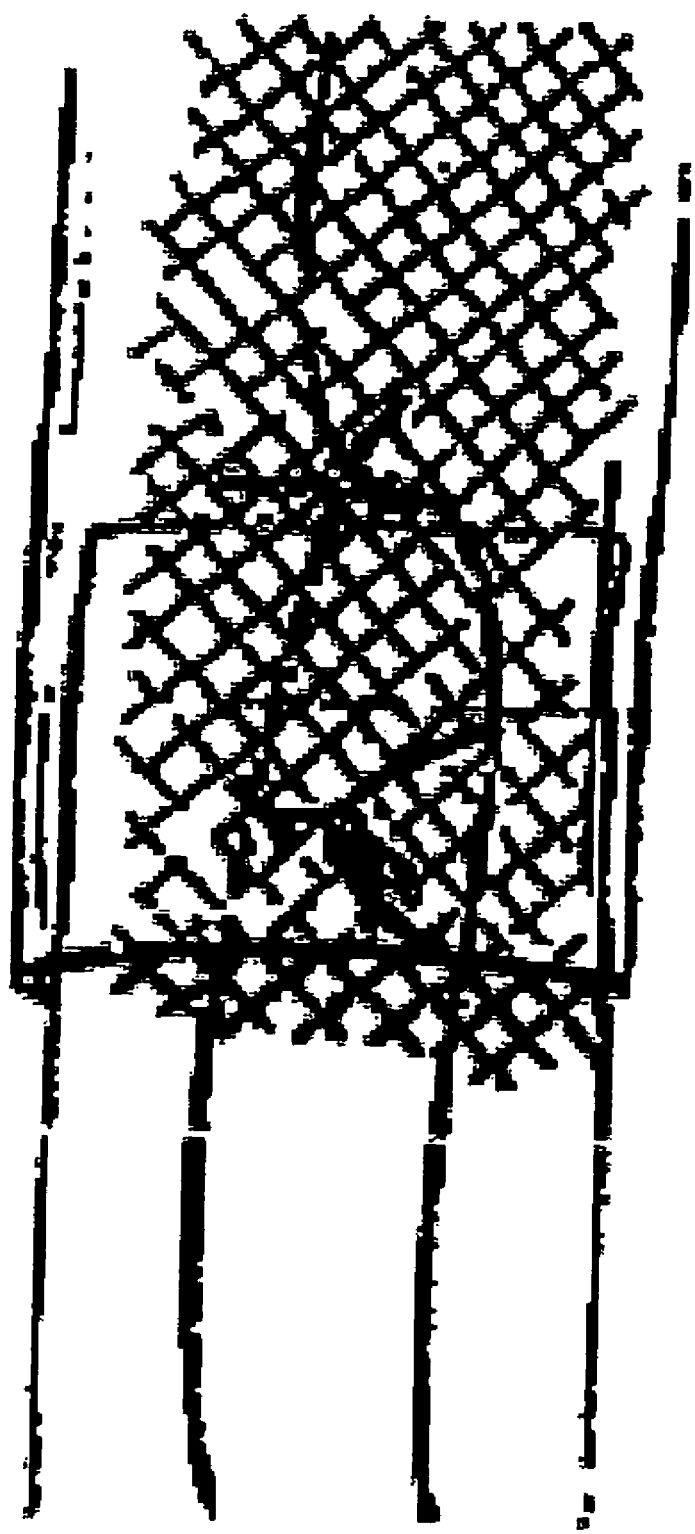
FIG. 12 is a fragmentary view of the support member combined with a sheath.

FIG. 11 discloses a tool 40 for securing dilator 36 onto tip 16 of needle 14. Tool 40 includes a first member 52 rotatably fastened to a second member 54 at a fulcrum 50. First member 52 is generally elongated and includes a first handle 48 at one end and a first support surface 42 at the other end. Similarly, second member 54 is generally elongated and includes a second handle 46 at one end and a second support surface 44 at the other end. In operation, dilator 36 can be supported by first support surface 42 while tip 16 is supported by second support surface 44. As handle 46 is moved closer to handle 48, needle tip 16 is secured to dilator 36, thereby enabling the support structure to be manipulated as the needles 14 are removed from the pelvic tissue.

Figure 18:
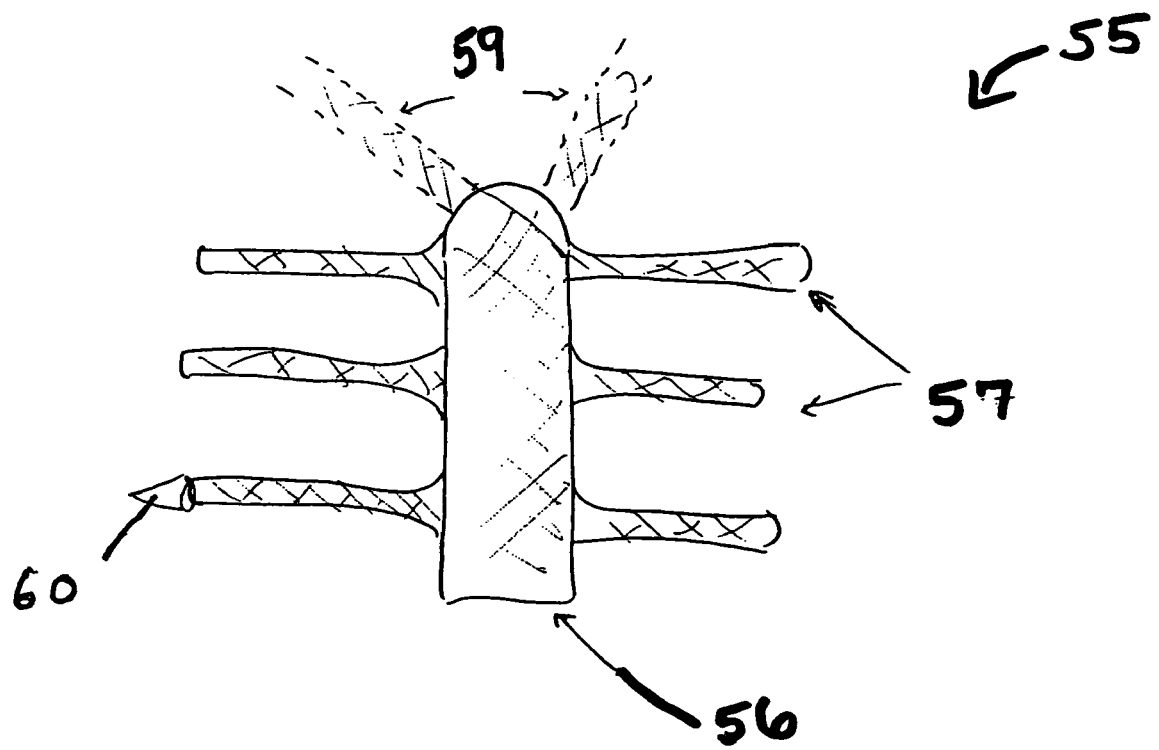
FIG. 18 is a top view of the self-fixating mesh implant of the present invention.

FIG. 18 discloses a self-fixating mesh implant of the present invention. The implant 55 includes a middle portion 56. The implant 55 also includes one or more pairs of legs 57 extending out from the middle portion 56 to the right and left. Posterior legs 59 may extend in a forward and/or rearward direction to provide needed support. The mesh may be fixed without the use of sutures either by relying on the properties of the mesh material itself or by adding a tissue anchor 60 to an end of at least one of the arms of the mesh.

Figure 19:
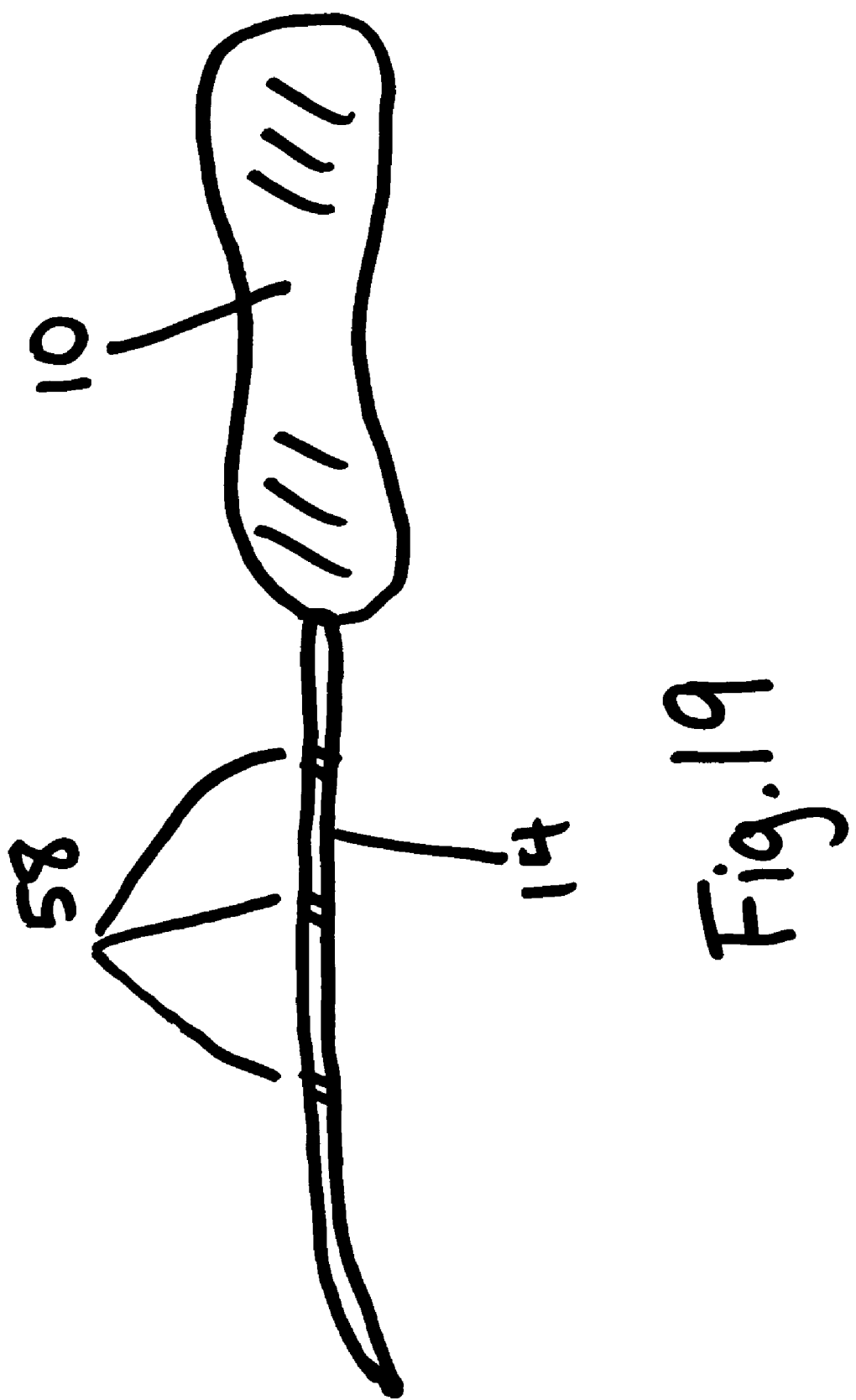
FIG. 19 illustrates a needle with marks for implantation of the self-fixating mesh of the present invention.

FIG. 19 discloses a tool for implanting the self-fixating mesh implant 55 of the present invention. The tool includes a handle 10 and a needle 14. The needle has markings 58 to indicate the depth for implantation of the implant 55, based on the anatomical placement for each leg. The needle tip is optionally adapted to connect to an anchor or dilator to ease placement of the mesh arms.

Numerous modifications and variations of the present invention are possible in light of the above teachings. It is understood that within the scope of the appended claims, the invention may be practiced other than as specifically described herein.

Obviously, numerous modifications and variations of the present invention are possible in light of the above teachings. It is therefore to be understood that within the scope of the appended claims, the invention may be practiced otherwise than as specifically described herein.

EXAMPLE OF METHOD

While many methods are contemplated herein, an example use of the method and apparatus of treating pelvic organ prolapse is disclosed, referring to FIGS. 12 through 24.

The procedure can be carried out under local or general anesthesia. An incision is made midline across the vaginal apex with sharp and blunt dissection to the ischial spine. Two small incisions are also made in the skin of the buttocks. Needles are passed from perianal skin incisions in the buttocks through the ischial rectal fossa to the vaginal incision.

The needle tip is palpated distal and inferior to the ischial spine prior to passage through the coccygeus muscle. Further dissection may be desired to aid palpation of the needle passage. Connectors are connected to each needle end. Needles are retracted and mesh is positioned. The mesh is then attached to the vaginal vault, and optionally to the lateral perirectal space or perineal body, tensioned, and the incisions are closed.

One embodiment of the present invention is a sterile, single use product consisting of two stainless steel curved needles and a polypropylene mesh implant. The same polypropylene mesh is available in an alternative configuration that allows the attachment of biological material.

Locking connectors on the ends of the mesh attach to each needle tip and are used to hold the mesh secure to the needle during passage of the mesh through the body. The connectors may be removed, if desired.

Four main preferred embodiments of the present apparatus are herein described. The physician may decide at his/her discretion which configuration is most appropriate for a particular patient.

A first embodiment (described herein as the tape embodiment) includes one-piece self-fixating mesh two removable plastic insertion sheaths over the mesh, and two locking connectors attached to the insertion sheaths. The tape is knitted polypropylene monofilament mesh that is pre-cut to 1.1 cm width×50 cm length with a non-absorbable or absorbable tensioning suture (polypropylene) threaded through the length to allow for tensioning adjustment after placement. The sheath affords convenient travel of the mesh through the tissue. Finger loops are formed by the sheath to allow for easy attachment of the connectors to the needle tips. The synthetic mesh tape is intended to remain in the body as a permanent implant.

A second embodiment (described herein as the cape embodiment) adds a 4 cm×13 cm mesh to the tape. This soft knitted mesh has large pores and is also made of polypropylene. The mesh is pre-attached to the tape and can be trimmed to suit surgical preference.

A third embodiment (described herein as the bio-cape embodiment) consists of two separate 1.1 cm×22 cm polypropylene mesh pieces, using the same material as in the tape version. However, one end has a locking connector and finger loop and the other end has a plastic clamp attached to a Y-shaped mesh used to facilitate attachment to a biological implant. The clamp is designed to facilitate the attachment of graft material with sutures.

In order to use the present invention in treatment of pelvic organ prolapse, the patient should initially be prepared by placing the patient in a modified dorsal lithotomy position with hips flexed, legs elevated in stirrups, and buttocks even with the edge of the table. Vaginal retraction may be used, if desired. Palpate the location of the ischial spines.

The fourth main embodiment of the present invention is a self-fixating mesh implant having a middle portion and several pairs of legs extending therefrom, in which the arms are designed to be fixed into supportive tissue by tissue anchors or by the material characteristics of the mesh itself.

The various embodiments require differing product preparations. Generally, the process includes steps to gain access to the target organ. For example, in treatment of posterior vaginal prolapse, the steps may include:

(1) Gaining access to the external vaginal vault using surgeon's preferred method of incision and dissection. If the cape is used, complete rectovaginal dissection may be required.

Figure 13:
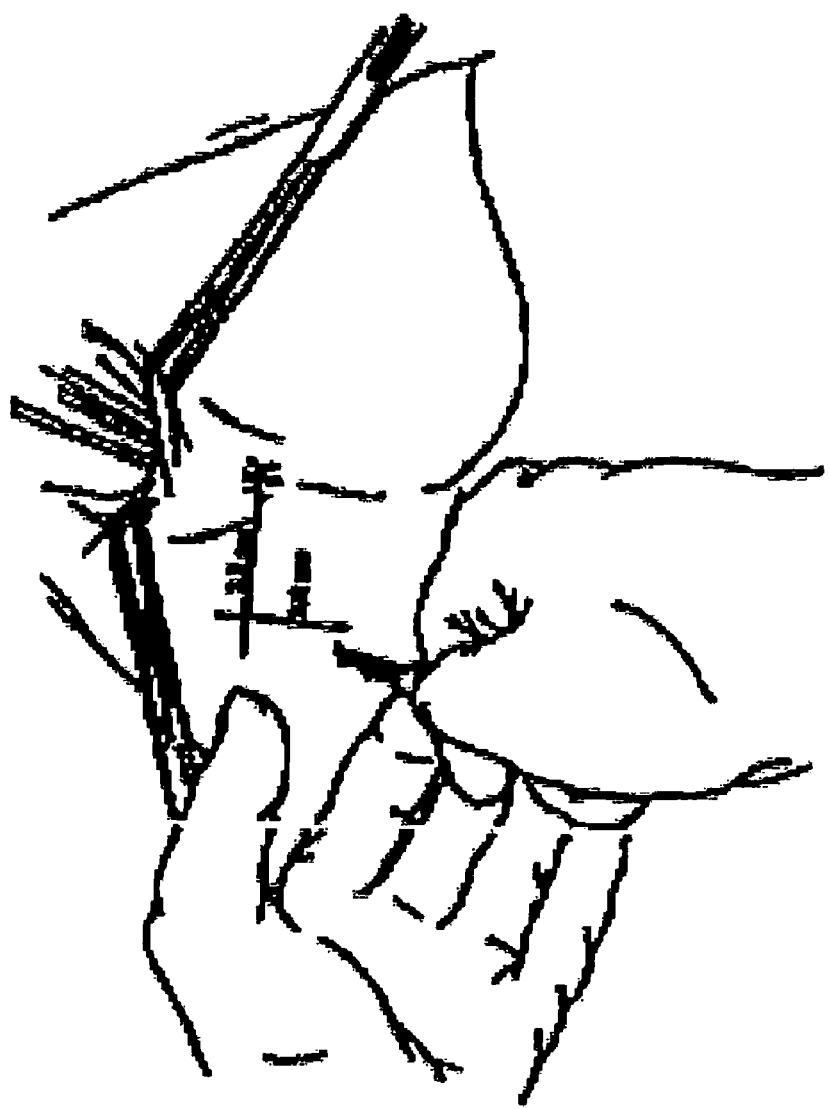
FIG. 13 illustrates the positioning of external incisions on the rectum of the patient.

(2) Making the appropriate incisions. In a preferred method, two small stab incisions are made on each side of the rectum approximately 3 cm lateral and 3 cm posterior to the anus, as shown in FIG. 13.

(3) Grasping the needle in one hand with the needle tip between the thumb and forefinger. Place the other hand near the needle bend. The two needles are identical. Either side may be done first.

Figure 14:
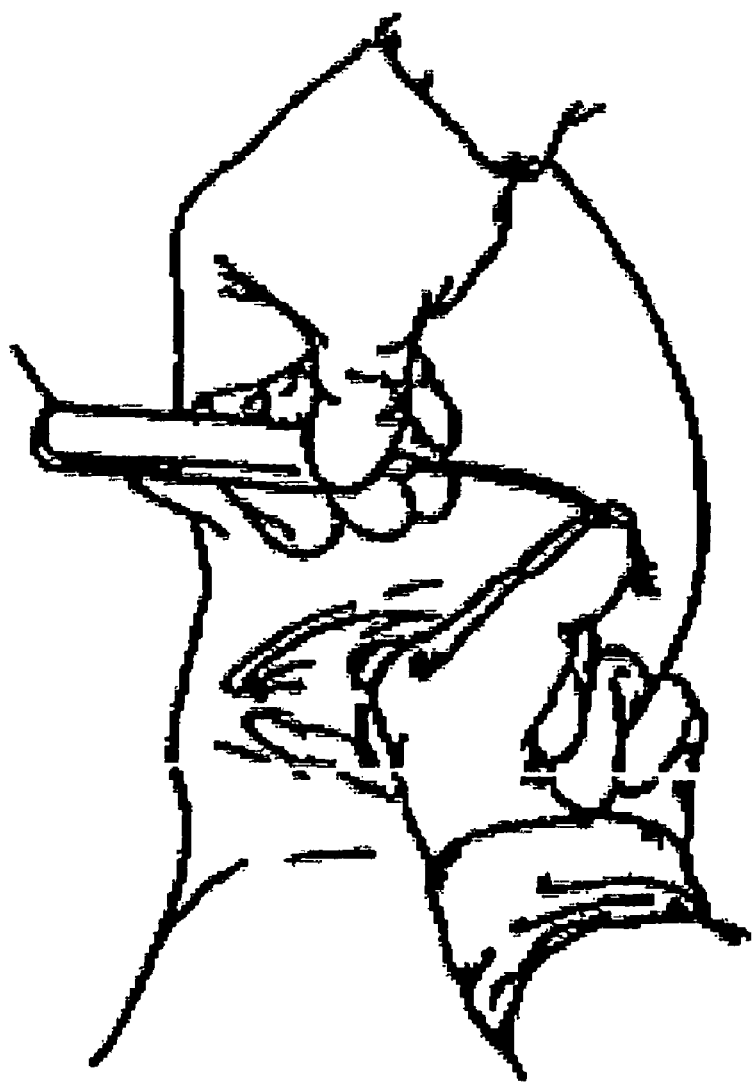
FIG. 14 illustrates a method of inserting the needle in a patient.

(4) Pointing the needle tip perpendicular to the skin with the handle pointing upward in a 12:00 position, as shown in FIG. 14.

(5) Directing the needle at a slight upward and lateral angle through the buttock. Puncture the initial layers of tissue by pushing on the needle bend until the needle enters the ischiorectal fossa.

Figure 15:
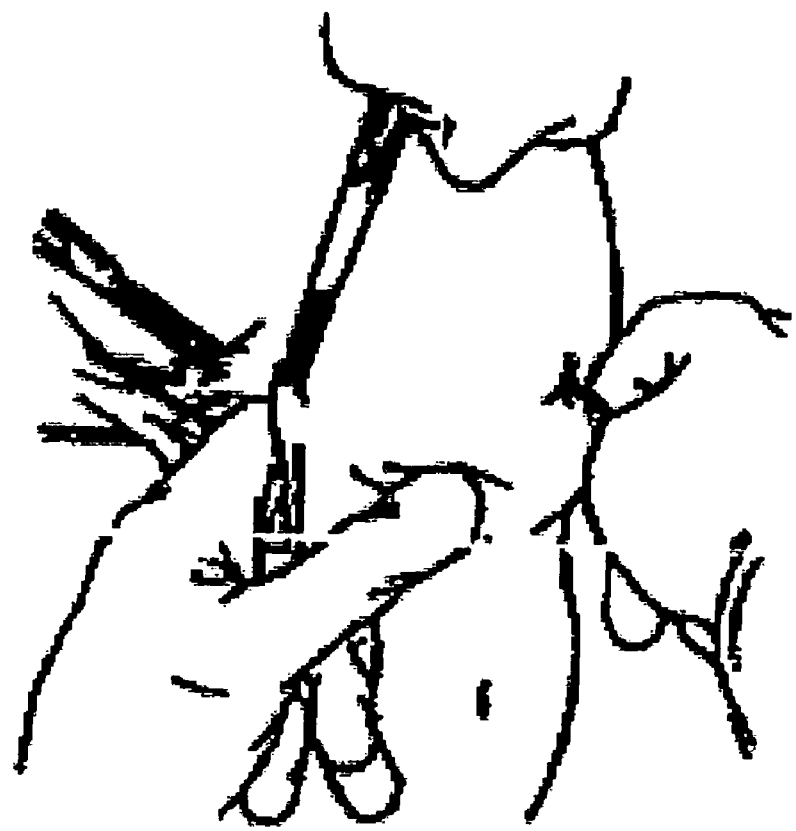
FIG. 15 illustrates palpation to aid passage of the needle to its appropriate position.

(6) Continuing to pass the needle tip lateral and parallel to the rectum toward the ischial spine. Palpate as needed, as shown in FIG. 15.

(7) Palpating the needle tip in front of the ischial spine. Penetrate the levator muscle advancing and lightly turning the needle tip medially toward the vaginal vault.

(8) Performing digital rectal exam to verify rectal integrity.

(9) Repeating steps 3-9 on patient's contralateral side.

Figure 16:
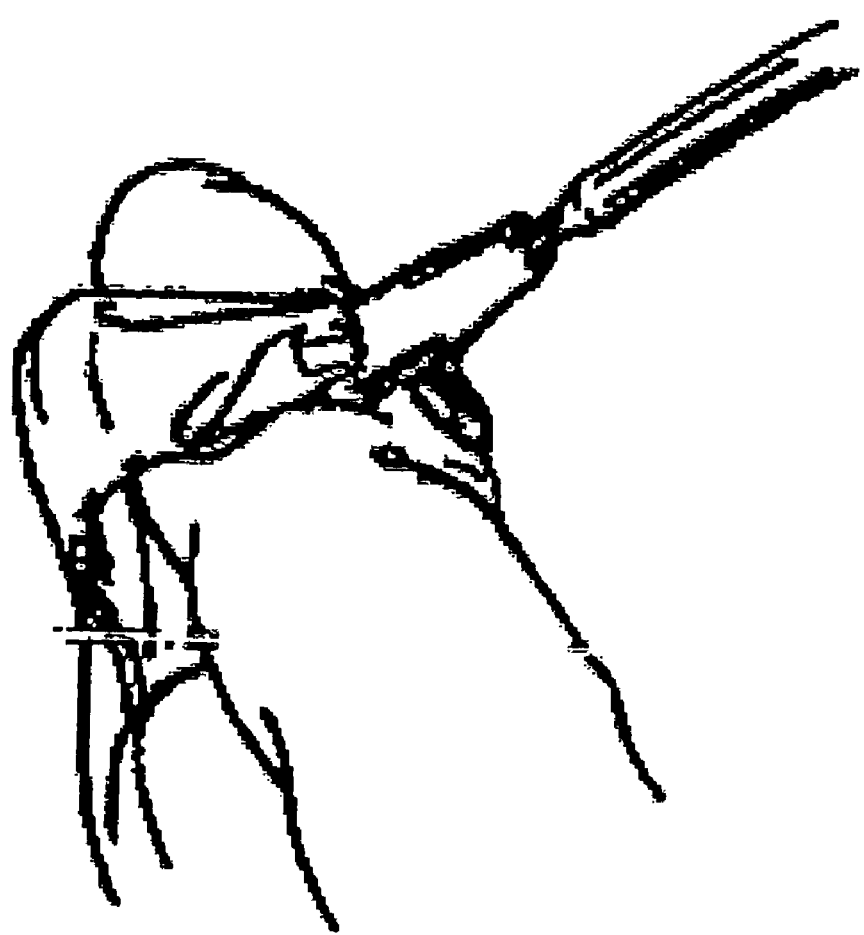
FIG. 16 illustrates an embodiment of the connector on the end portion of the mesh.

(10) Inserting a finger into the loop behind the connector on the mesh, as shown in FIG. 16. Insert the connector into the vagina. Snap onto the needle tip.

(11) Pulling each needle and connector back through the skin incision. Adjust the sheath and mesh into an approximate position.

(12) Cutting the needles from the mesh near the end of the sheath, below the blue dots provided to guide the surgeon.

(13) Attaching the mesh to the exterior apex of the vaginal wall with two or more sutures.

(14) Ensuring the vaginal wall is in the appropriate anatomic position. If the cape is being used, lay the cape in the perirectal space, in a tension-free manner, and close the perirectal fascia over the mesh or the vaginal incision.

Figure 17:
FIG. 17 illustrates positioning of the mesh by manipulating the sheathed end portions.

(15) Pulling on the mesh assemblies to make final adjustments, as shown in FIG. 17.

(16) Removing plastic sheaths.

(17) Trimming the mesh at the level of the subcutaneous tissue.

(18) Closing the incisions.

(19) Using a vaginal pack and antibiotic prophylaxis as appropriate.

As an alternative embodiment, the invention may include a kit, apparatus, and method with only one needle. In these alternative embodiments, it is necessary to:

(1) Gain access to the external vaginal vault using surgeon's preferred method of incision and dissection. If the cape is used, complete rectovaginal dissection is required.

(2) Make two small stab incisions on each side of the rectum approximately 3 cm lateral and 3 cm posterior to the anus, as shown in FIG. 13.

(3) Grasp the needle in one hand with the needle tip between the thumb and forefinger. Place the other hand near the needle bend.

(4) Point the needle tip perpendicular to the skin with the handle pointing upward in a 12:00 position, as shown in FIG. 14.

(5) Direct the needle at a slight upward and lateral angle through the buttock. Puncture the initial layers of tissue by pushing on the needle bend until the needle enters the ischiorectal fossa.

(6) Continue to pass the needle tip lateral and parallel to the rectum toward the ischial spine. Palpate as needed, as shown in FIG. 15.

(7) Palpate the needle tip in front of the ischial spine. Penetrate the levator muscle advancing and lightly turning the needle tip medially toward the vaginal vault.
(8) Perform digital rectal exam to verify rectal integrity.
(9) Repeat steps 3-9 with the single needle on the patient's contralateral side.
(10) Insert a finger into the loop behind the connector on the mesh, as shown in FIG. 16.
(11) Pull the needle and connector back through each skin incision. Adjust the sheath and mesh into an approximate position.
(12) Attach the mesh to the exterior apex of the vaginal wall with two or more sutures.
(13) Ensure the vaginal wall is in the appropriate anatomic position. If the cape is being used, lay the cape in the perirectal space, in a tension-free manner, and close the perirectal fascia over the mesh or the vaginal incision.
(14) Pull on the mesh assemblies to make final adjustments, as shown in FIG. 17.
(15) Remove plastic sheaths.
(16) Trim the mesh at the level of the subcutaneous tissue.
(17) Close the incisions.
(18) Use the vaginal pack and antibiotic prophylaxis as appropriate.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An apparatus for treating pelvic organ prolapse in a patient utilizing a posterior perirectal tissue pathway comprising:
    a support portion adapted to be placed in a therapeutically effective position, including first and second ends;
    a first elongated end portion connected to said first end of said support portion, wherein the first elongated end portion includes a first dilator configured to attach securely with a tip of a needle;
    a second elongated end portion connected to said second end of said support portion, wherein the second elongated end portion includes a second dilator configured to attach securely with a tip of a needle;
    a first needle including a straight portion, a tip, and a curved portion between the straight portion and the tip, the curved portion having a first radius of curvature, and a second radius of curvature distinct from the first radius of curvature, wherein the first radius of curvature of the first needle is between the tip of the first needle and the second radius of curvature of the first needle, and the first radius of curvature of the first needle is between about 2 inches and about 4 inches and the second radius of curvature of the first needle is between about 4 inches and about 6 inches.

2. The apparatus of claim 1, further comprising:
    a second needle comprising a straight portion, a tip, and a curved portion between the straight portion and the tip, the curved portion having a first radius of curvature, and a second radius of curvature distinct from the first radius of curvature, wherein the first radius of curvature is between the tip of the second needle and the second radius of curvature of the second needle, and the first radius of curvature is between about 2 inches and about 4 inches and the second radius of curvature is between about 4 inches and about 6 inches.

3. The apparatus of claim 2, wherein the straight section of the first needle is between about 5 inches and about 7 inches.

4. The apparatus of claim 3, wherein the straight section of the first needle is between about 5.5 inches and about 6.5 inches.

5. The apparatus of claim 3, wherein the straight section of the first needle is between about 4.5 inches and about 5.5 inches.

6. The apparatus of claim 2, further comprising a tool for connecting the tip of the first needle to the dilator of the first elongated portion.

7. The apparatus of claim 2, further comprising:
    a first transition zone disposed between the first elongated end portion and the first dilator; and,
    a second transition zone disposed between the second elongated portion and the second dilator,
    wherein the first transition zone and the second transition zone are each comprised of a riveted synthetic cape which provides a tapered transition from respective end portion to dilator.

8. The apparatus of claim 1, further comprising a repositioning means to effect tightening or loosening said apparatus without adversely affecting the therapeutic efficacy of said apparatus.

9. The apparatus in claim 8, wherein said repositioning means comprises at least one filament threaded along at least one end portion.

10. The apparatus of claim 1, wherein the diameter of said first needle is between about 0.100 inches and about 0.150 inches.

11. The apparatus of claim 1, wherein the straight section of the first needle is between about 3 inches and about 7 inches.

12. A kit for repairing pelvic organ prolapse in a patient utilizing a posterior perirectal tissue pathway comprising:
    a support member comprising a support portion and two end portions, wherein at least one of said end portions further comprises a removable plastic sheath;
    a first needle comprising a first handle, a first tip, a straight portion, and a curved portion between the straight portion and the tip, the curved portion having a first radius of curvature, and a second radius of curvature different from the first radius of curvature, wherein the first radius of curvature of the first needle is between the tip of the first needle and the second radius of curvature of the first needle, and the first radius of curvature of the first needle is between about 2 inches and about 4 inches and the second radius of curvature of the first needle is between about 4 inches and about 6 inches, and the first needle is configured to form a first pathway through tissue adjacent to said prolapsed organ, said pathway extending between an external perirectal region and a region of an ischial spine of the patient.

13. The kit of claim 12, further comprising:
    a second needle comprising a second handle, a second tip, a straight portion, and a curved portion between the straight portion and the tip, the curved portion having a first radius of curvature, and a second radius of curvature different from the first radius of curvature, wherein the first radius of curvature of the second needle is between the tip of the second needle and the second radius of curvature of the second needle, and the first radius of curvature of the second needle is between about 2 inches and about 4 inches and the second radius of curvature of the second needle is between about 4 inches and about 6 inches, and the second needle is configured to form a second pathway through tissue adjacent to said prolapsed organ, said pathway extending between an external perirectal region and a region of an ischial spine of the patient.

14. The kit of claim 13, wherein the first radius of curvature of the first needle is located on the same side of the first needle as the second radius of curvature.

15. The kit of claim 14, wherein the first radius of curvature of the second needle is located on the same side of the second needle as the second radius of curvature.

16. The kit of claim 13, wherein the first radius of curvature of the first needle is located on the opposite side of the first needle from the second radius of curvature.

17. The kit of claim 16, wherein the first radius of curvature of the second needle is located on the opposite side of the second needle from the second radius of curvature.

* * * * *